(12) United States Patent
Bouhassira et al.

(10) Patent No.: US 6,534,314 B1
(45) Date of Patent: Mar. 18, 2003

(54) METHODS AND COMPOSITIONS FOR TRANSFORMING CELLS

(75) Inventors: Eric Bouhassira, Hastings on Hudson, NY (US); Philippe Leboulch, Charlestown, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/293,303

(22) Filed: Apr. 16, 1999

Related U.S. Application Data

(63) Continuation of application No. PCT/US97/09954, filed on Jun. 6, 1997, which is a continuation-in-part of application No. 08/743,796, filed on Nov. 5, 1996, now Pat. No. 5,928,914, which is a continuation of application No. 08/664,084, filed on Jun. 14, 1996, now abandoned.

(51) Int. Cl.[7] .............................................. C12N 15/90

(52) U.S. Cl. ....................... 435/462; 435/440; 435/463; 536/24.1

(58) Field of Search ................................. 435/440, 462, 435/69.1, 91.4, 455, 463, 450, 320.1, 325; 536/24.1; 514/44; 424/93.1

(56) References Cited

U.S. PATENT DOCUMENTS

| | | | | |
|---|---|---|---|---|
| 4,959,317 A | | 9/1990 | Sauer ........................ | 435/462 |
| 5,262,128 A | * | 11/1993 | Leighton et al. ............ | 422/100 |
| 5,654,182 A | * | 8/1997 | Wahl et al. ............... | 435/172.1 |
| 5,888,732 A | | 3/1999 | Hartley et al. ................. | 435/6 |
| 6,171,861 B1 | * | 1/2001 | Hartley et al. .............. | 435/455 |

FOREIGN PATENT DOCUMENTS

| | | |
|---|---|---|
| EP | 0300422 A | 1/1989 |
| WO | WO 9706271 A | 9/1990 |
| WO | WO 9309239 A | 5/1993 |

OTHER PUBLICATIONS

Eric E. Bouhassira et al, Transcriptional Behavior of LCR Enhancer Elements Integrated at the Same Chromosomal Locus by Recombinase–Mediated Cassette Exchange, Blood, vol. 90, No. 9, (11/01) 1997:pp. 3332–3344.*

Rose et al., Methods in Enzymology vol. 185 (1990), Gene Expression Technology Edited By David V. Goeddel, pp. 234–279.*

Bethke et al, "Segmental genomic replacement by Cre–mediated recombination:", Nucleic Acids Research, vol. 25 (14), pp. 2828–2834, Jul. 1997.*

Feng, Y.Q. et al., "High–efficiency recombinase–mediated cassette exchange," 40th Annual Meeting of the American Society of Hematology, Miami, FL, Dec. 4–8, 1998. (Also presented at a meeting at Cold Spring Harbor Laboratories entitled "The conditional Genetic Technologies in the Monse Workshop," Aug. 31–Sep. 2, 1998).

Abremski et al. (1983), "Studies on the Properties of P1 Site–Specific Recombination: Evidence for Topologically Unlinked Products Following Recombination", *Cell* 32:1301–1311.

Argos et al. (1986), "The Integrase Family of Site–Specific Recombinases: Regional Similarities and Global Diversity", *The EMBO Journal* 5:433–440.

Bouhassira, E. E. et al. (1996), "Recombinase–mediated–cassette–exchange (RMCE): A novel technique for integration of single copy of transgenes at pre–determined chromosomal sites. Application to the study of the human beta–globin LCR", Abstract No. 749, Thirty–eight Annual Meeting of the American Society of Hematology, Orlando, Florida, USA, Blood 88 (10 Suppl. 1 Part 1–2), 190A.

Choulika, A. et al. (1996), "Transfer of Single Gene–Containing Long Terminal Repeats Into The Genome of Mammalian Cells By A Retroviral Vector Carrying the CRE Gene and the LOXP Site", *Journal of Virology*, 70(3):1792–1798.

Hoess et al. (1982), "P1 Site–Specific Recombination: Nucleotide Sequence of the Recombining Sites", *Proc. Natl. Acad. Sci. USA* 79:3398–3402.

Hoess et al. (1990), "The Cre–lox Recombination System", *Nucleic Acids and Molecular Biology* 4:99–109.

Leboulch, P. et al. (1996), "Retrovirus and Cre–Lox–mediated Integration (RCLI): A two–step gene transfer procedure for efficient chromosomal integration of large DNA fragments", Abstract No. 2379, Thirty–eighth Annual Meeting of the American Society of Hematology, Orlando, Florida, USA, Blood 88 (10 Suppl. 1 Part 1–2), 688A.

Sauer (1993), "Manipulation of Transgenes by Site–Specific Recombination: Use of Cre Recombinase", *Methods in Enzymology* 225:890–900.

Sauer et al. (1988), "Site–Specific DNA Recombination in Mammalian Cells by the Cre Recombinase of Bacteriophage P1", *Proc. Natl. Acad. Sci. USA* 85:5166–5170.

Schlake et al. (1994), "Use of Mutated FLP Recognition Target (FRT) Sites for the Exchange of Expression Cassettes at Defined Chromosomal Loci", *Biochemistry* 33:12746–12751.

(List continued on next page.)

*Primary Examiner*—David Guzo
*Assistant Examiner*—Bronwen M. Loeb
(74) *Attorney, Agent, or Firm*—Lahive & Cockfield, LLP; Jane E. Remillard, Esq.; Richa Nand, Esq.

(57) ABSTRACT

Methods and compositions for transforming cells, resulting in efficient and stable site-specific integration of transgenes, are disclosed. Transformation is achieved by providing an acceptor DNA containing two inverted lox sequences and a donor DNA containing the same two inverted lox sequences, and then contacting the acceptor and donor DNA with a recombinase (e.g., Cre or Flp) which causes recombination at the lox sequences contained in the DNAs. Prior to recombination, the acceptor DNA is preferably integrated into the genome of a cell, such as an embryonic stem cell or a fertilized egg. The acceptor DNA optionally may further contain a negatively selectable marker to allow for screening of cells which have undergone the desired site-specific recombination (e.g., DNA cassette exchange).

16 Claims, 10 Drawing Sheets

OTHER PUBLICATIONS

Schubeler, D., et al., (1997) Excision Of An Integrated Provirus By The Action Of FLP Recombinase, *In Vitro Cell. Dev. Biol.–Animal*, vol. 33, pp. 825–830.

Schubeler, D., et al. , (1998)"Retargeting of Retroviral Interagration Sites for the Predictable Expression of Transgenes and the Analysis of Cis–Acting Sequences", *Biochemistry*, vol. 37, pp. 11907–11914.

Seibler, J., et al.,(1998)"DNA Cassette Exchange in ES Cells Mediated by FLP Recombinase: An Efficient Strategy for Repeated Modification of Tagged Loci by Marker–Free–Constructs", *Biochemistry*, vol. 37, pp. 6229–6234.

Waterhouse et al. (1993), "Combinatorial Infection and In Vivo Recombination": A Strategy for Making Large Phage Antibody Repertoires, *Nucleic Acids Research* 9:2265–2266.

Wang, P. et al. (1995), "High Frequency Recombiantion Between LOXP Sites In Human Chromosomes Mediated By an Adenovirus Vector Expressing CRE Recombinase", *Somatic Cell and Molecular Genetics* 21(6):429–441.

* cited by examiner

PRINCIPLE OF RMCE

METHODS AND COMPOSITIONS FOR TRANSFORMING CELLS

RELATED APPLICATIONS

This application is a continuation-in-part of U.S. patent application Ser. No. 08/743,796, filed on Nov. 5, 1996, now U.S. Pat. No. 5,929,914 which is a continuation of U.S. patent application Ser. No. 08/664,084, filed on Jun. 14, 1996 now abandoned, and is a CON of PCT/US97/09954 filed Jun. 6, 1997. The complete contents of these patent applications are hereby incorporated by reference herein.

GOVERNMENT FUNDING

This invention was made with government support under grants HL38655, HL 554350, DK54071-020 and HL07556, all of which were awarded by the NIH. The United States government has certain rights in the invention.

BACKGROUND OF THE INVENTION

The success of gene therapy techniques depends largely on the ability to achieve a combination of stable chromosomal integration and high-level, regulated expression of transferred genes. Regulated gene expression is most easily achieved by means of large DNA fragments containing extensive cis-acting regulatory regions. For example, gene therapy for β-globin disorders may require high-level, position-independent expression of extended gene and LCR sequences.

Many current techniques allow efficient transient transfection of cells in vitro and in vivo with large DNA fragments. However, subsequent chromosomal integration is very inefficient. To overcome low levels of integration, retroviral vectors which integrate very efficiently in permissive cells can be used. However, such vectors are greatly limited by constraints of size and sequence composition.

There are also many other techniques available for stable integration of transgenes in mammalian cells (Kriegler, M. (1990) *Gene Transfer and Expression. A Laboratory Manual*, Stockton Press, New York); and (Wolf, J. A. (1994) *Gene Therapeutics: Methods and Application of Direct Gene Transfer*, Birkhauser, Boston). However, these methods result in integration at random chromosomal locations of an uncontrolled number of transgene copies that express at levels that generally cannot be predicted or reproduced with precision because of position-effects. The inability to control the site of integration, the number of integrated copies and the level of expression of transgenes has impeded progress in studies of both gene expression and the physiological effects of transgenes.

Systems which can perform site-specific chromosomal integration efficiently therefore have wide utility. The first site-specific chromosomal integrations in mammalian cells were based on integration of a single Lox or FRT site on a chromosome followed by trapping of rare integration events (O'Gorman et al. (1991) *Science* 251:1351–1355; and Sauer, B. (1994) *Current Opinion in Biotechnology* 5:521–527). These pioneering methods had three limitations: 1) they were quite inefficient, 2) the entire plasmid was integrated, and 3) a positive selectable marker was left in the chromosome after the integration. The low efficiency of these methods is due to the reversibility of the recombination reaction: after integration the transgene is re-excised if the two identical Lox or FRT sites that flank the transgene recombine with each other. Since the excision reaction is intra-molecular while the insertion reaction is inter-molecular, excisions are favored.

U.S. Pat. No. 4,959,317 discloses the use of Cre-Lox site-specific recombination to achieve gene transfer in eukaryotic cells (Sauer et al. (1993) *Methods in Enzymology* 225: at 898). The target site of the CRE recombinase is a 34 bp sequence that consists of two inverted 13 bp CRE-binding sites separated by an eight base spacer within which the recombination occurs (Hoess, et al. (1984) *Proc. Nat. Acad. Sci.* (USA) 81:1026–1029).

Additional site-specific DNA recombination systems which provide more efficient and stable integration of transgene sequences into genomic DNA, preferably without the use of a positively selectable marker, would be greatly beneficial.

SUMMARY OF THE INVENTION

The present invention provides methods and compositions for achieving efficient and stable site-specific DNA recombination using a recombinase/lox system, such as the Cre/lox system or the Flp/frt system. In one embodiment, the method comprises contacting a recombinase (e.g., Cre or Flp) with (a) an acceptor vector comprising two incompatible lox sequences, L1 and L2, and (b) a donor vector comprising a selected DNA flanked by the L1 and L2 sequences, or sequences which are compatible with the L1 and L2 sequences, thereby causing transfer of the selected DNA from the donor vector into the acceptor vector by recombination at the compatible lox sequences. In a preferred embodiment, the acceptor vector is a retroviral vector or an adeno-associated vector.

In another embodiment, the invention provides a method of transforming a cell with a selected DNA comprising, in any order, the steps of introducing into the cell an acceptor vector which integrates into the genome of the cell, the acceptor vector comprising two incompatible lox sequences, L1 and L2, (b) introducing into the cell a donor vector comprising the selected DNA flanked by the L1 and L2 sequences, or sequences which are compatible with the L1 and L2 sequences, and (c) contacting L1 and L2 with a recombinase, such as Cre or Flp, thereby causing transfer of the selected DNA from the donor vector into the acceptor vector. The recombinase can be introduced into the cell in the form of a protein or a gene encoding the protein.

In another embodiment, the invention provides a vector selected from the group consisting of retroviral vectors and adeno-associated vectors comprising two incompatible lox sequences, L1 and L2.

In another embodiment, the invention provides a method of achieving site-specific recombination by providing a donor DNA comprising two inverted lox sequences, and an acceptor DNA comprising the same two inverted lox sequences contained in the donor DNA, and then contacting the donor and acceptor DNA with a recombinase (e.g., Cre or Flp). Preferably, the acceptor DNA is integrated into the genome of a host cell prior to contact with the recombinase (e.g., by homologous recombination), so that recombination results in site-specific genomic integration of a desired transgene or other polynucleotide. In another preferred embodiment, the donor DNA is present in excess of the acceptor DNA. Suitable lox sequences comprise the nucleotide sequences of SEQ ID NO:1, SEQ ID NO:2 and inversions thereof. The donor and acceptor DNAs can further contain selectable markers which are generally positioned between the two inverted lox sequences to help select for cells which have undergone the desired recombination.

The methods and compositions of the invention can be used in methods of in vivo and In vitro gene transfer (e.g., gene therapy) to cause efficient and stable site-specific (targeted) integration of transgene sequences. By controlling the site or position of integration of a transgene into the genome of a cell, expression levels can be predictably determined. For example, in cells, the invention can be used to produce desired proteins (e.g., drugs) by insertion of transgenes at pre-selected chromosomal locations where expression of the transgene will be high. Similarly, the invention can be used to develop "designer proteins" by insertion of multiple versions of a gene or DNA (e.g., related variants) at the same locus to test the various versions of proteins produced in a context in which the proteins are all produced in the same amount. The invention can also be used to study and to identify genetic elements that control position effects.

In addition, the invention can be used in vivo to create transgenic mammals and/or plants. For example, animal models of human disease can be generated, particularly if multiple genes have to be expressed at well regulated levels. Animals and/or plants can be created which contain target lox sequences (e.g., inverted or incompatible) at chromosomal locations that are not subject to position effects or to desired position effects for directing expression of a gene of interest. This allows for the generation of animal models and/or plants with, for example, higher resistance to disease or improved physical/functional characteristics.

DETAILED DESCRIPTION OF THE INVENTION

Figure 1:
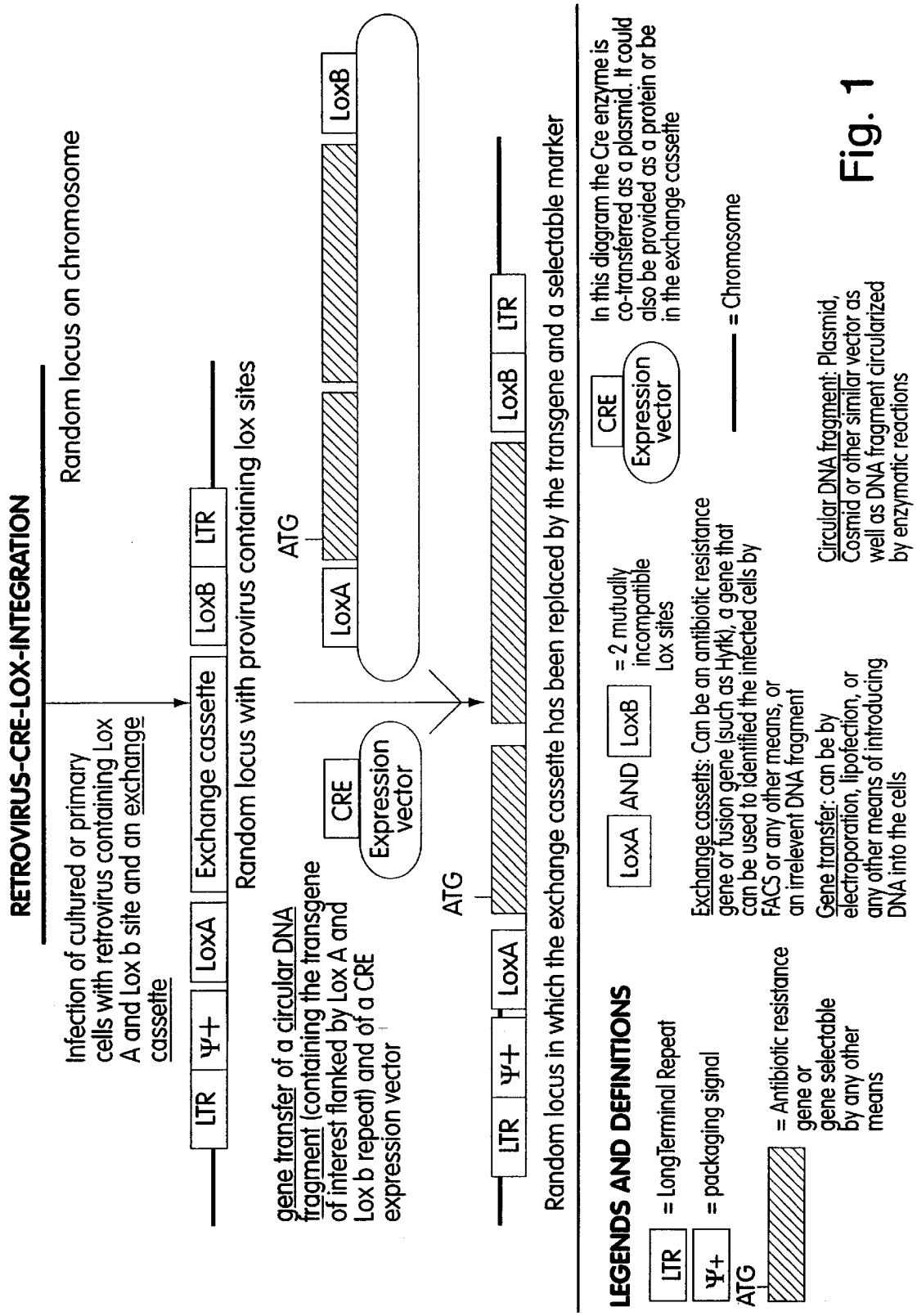
FIG. 1 is a schematic illustration of Cre/lox mediated gene transfer. Lox A and Lox B are mutually incompatible lox sites which are unable to recombine with each other in the presence of Cre recombinase.

The present invention provides methods and compositions for causing efficient site-specific DNA recombination, for example, in cells or fertilized eggs. The advantages over current cell transformation techniques provided by the invention include highly efficient and stable integration of large DNA sequences, such as transgene sequences, into chromosomal DNA, without the need for a selectable marker in the integrated DNA. In one embodiment, the method of the invention comprises contacting a recombinase, such as Cre, with (a) an acceptor DNA (e.g., vector) comprising two incompatible lox sequences, L1 and L2, and (b) a donor DNA (e.g., vector) comprising a selected DNA flanked by the L1 and L2 sequences, or lox sequences which are compatible with the L1 and L2 sequences, thereby causing transfer of the selected DNA from the donor vector into the acceptor vector by recombination at the compatible lox sequences.

In another embodiment, the method of the invention comprises contacting a recombinase, such as Cre or Flp, with (a) a donor DNA comprising two inverted lox sequences, and (b) an acceptor DNA comprising the same two inverted lox sequences contained in the donor DNA. Preferably, the acceptor DNA is integrated into the genome of a host cell (e.g., by homologous recombination), prior to contact with the recombinase so that recombination results in site-specific genomic integration of a desired transgene or other polynucleotide.

The term "site-specific recombination," refers to DNA transfer from a donor DNA or vector to an acceptor DNA or vector.

The term "lox sequence" refers to a nucleotide sequence which undergoes recombination (e.g., DNA cross-over and exchange) when catalyzed by a recombinase, such as Cre, Flp or another member of the Int family of recombinases (Argos et al. (1986) *EMBO J.* 5: 433). Suitable lox sequences include, for example, the lox sequences recognized by Cre recombinase, and the frt sequences recognized by Flp recombinase.

The term "recombinase" refers to any recombinase capable of catalyzing a site-specific recombination at a lox site. Suitable recombinases include, for example, Cre recombinase (Sauer et al. (1993) *Methods in Enzymology* 225: 898) and Flp recombinase (Buchholz et al. (1996) *Nucl. Acids Res.* 24:4256–4262; Buchholz et al. (1998) *Nat. Biotechnol.* 16:657–662).

The term "incompatible lox sequences" refers to two or more lox sequences (referred to herein as L1 and L2) which differ from one another and, therefore, can not undergo recombination with one another. For example, lox sequences can be rendered incompatible if their nucleotide sequences differ by even one nucleotide, particularly in their spacer regions. In contrast, the term "compatible lox sequences" refers to two or more lox sequences which can recombine when catalyzed to do so by a recombinase.

The term "inverted lox sequences" refers to two or more substantially identical lox sequences (referred to herein as L1 and 1L) which are positioned in the reverse orientation with respect to one another so that recombination between the L1 and 1L sequences within the same (e.g., acceptor) DNA (e.g., intrachromosomal recombination) leads to an inversion of the intervening sequence, as opposed to an excision (see FIG. 4). "Inverted lox sequences" of the invention recombine with the same lox sequences (e.g., contained within a separate donor DNA) at the same frequency (i.e., specific activity) because they are made up of identical or substantially identical nucleotide sequences. Overall, these features provide a site-specific recombination system which results in (1) substantially equal amounts of intermolecular recombination between identical L1 or 1L sequences (e.g., contained on separate acceptor and donor DNAs), and (2) substantially no excision from intramolecular recombination between inverted L1 and 1L sequences (e.g., contained within the same acceptor or donor DNA). As shown schematically in FIG. 4, this allows for highly (up to 100%) efficient and stable recombinase-mediated DNA integration.

The terms "acceptor DNA" and "acceptor vector," are used interchangeably herein and refer to any DNA or vector which, preferably, is capable of integrating into the genome of a cell. For example, the acceptor DNA or vector can be of viral origin, such as a retroviral vector or adeno-associated vector. Generally, the acceptor DNA or vector contains an exchange cassette (i.e., DNA which is replaced by DNA from the donor vector) and can also, optionally, contain a selectable (e.g., negative) marker gene.

The terms "donor DNA" and "donor vector" are used interchangeably herein and refer to any DNA or vector (e.g., circular plasmid DNA) containing DNA which is transferred to the acceptor DNA or vector via a recombinase-mediated exchange reaction. Generally, the donor DNA or vector comprises plasmid DNA and, optionally, also can contain a selectable (e.g., positive) marker gene.

The method of the present invention utilizes a recombinase-mediated exchange reaction which takes place between identical or compatible (i.e., able to recombine with one another) lox sequences. The efficient exchange of DNA between identical or compatible lox sequences enables transfer of DNA from the donor to the acceptor vector, which each contain identical or compatible lox sites (see FIG. 4). However, once transferred from donor to acceptor vector (i.e., intermolecular transfer), the transferred DNA is stabilized or "locked" into place. In one embodiment, this is achieved by using incompatible lox sequences (e.g., L1 and L2) within the acceptor vector which prevent intramolecular exchange and excision of the transferred DNA. In another embodiment, this is achieved by using identical inverted lox sequences (e.g., L1 and 1L) within the acceptor vector which recombine with each other in reverse so that the transferred DNA is inverted within the vector without excision of the transferred DNA. Therefore, the transferred DNA is integrated in a highly efficient and stable manner.

In addition to effective and stable DNA exchange reactions, the methods of the present invention take advantage of highly efficient integration vectors, such as retroviral vectors, adeno-associated vectors, or vectors encoding retroviral integrases, for use in integrating acceptor DNA into the genome of a cell. The studies described herein demonstrate that such vectors are compatible for use with site-specific DNA transfer systems, such as recombinase/lox systems.

The invention also employs an excess of donor DNA relative to acceptor DNA so that intermolecular exchange leading to insertion of donor DNA into (e.g., genomically integrated) acceptor DNA occurs at a higher frequency that intramolecular exchange (e.g., within acceptor DNA) leading to excision of donor DNA.

Overall, the site-specific recombination system of the invention provides a means for highly efficient and stable DNA transfer which can be used, for example, in methods of gene therapy, gene expression control, and transgenic applications. For example, as described herein, the methods and compositions of the present invention can be used to achieve a 100 to 10,000 fold increase in transgene integration and expression compared to random integration which occurs in the absence of site-specific recombination. The invention further provides a way to achieve site-specific recombination without the incorporation of selectable markers into the genome following exchange.

Accordingly, in another embodiment, the invention provides a method of transforming a selected cell or tissue, such as a mammalian cell (e.g., embryonic stem cell) or fertilized egg, with a desired DNA. The method comprises the steps of (a) introducing into the cell or tissue an acceptor vector comprising two incompatible lox sequences, L1 and L2, (b) introducing into the cell a donor vector comprising the selected DNA flanked by the L1 and L2 sequences, or lox sequences which are compatible with the L1 and L2 sequences, and (c) contacting L1 and L2 with a recombinase, such as Cre, to cause transfer of the selected DNA from the donor vector into the acceptor vector (by way of an exchange reaction between the compatible lox sequences). While not essential, the acceptor vector is preferably introduced into the cell prior to introduction of the donor vector, so that the acceptor vector has integrated into the host genome prior to DNA exchange with the donor vector.

Alternatively, selected cells and/or tissues can be transformed by (a) introducing into the cell or tissue an acceptor DNA comprising two inverted lox sequences; (b) introducing into the cell or tissue a donor DNA comprising the same two inverted lox sequences contained in the acceptor DNA; and (c) contacting the donor and acceptor DNA with a recombinase. The recombinase can be introduced into the cell or tissue in the form of an exogenous protein or in the form of a gene encoding the recombinase which is expressed in the cell or tissue following transfection. Suitable lox sequences again include those having the nucleotide sequences shown in SEQ ID NOS: 1 and 2, as well as inversions thereof.

The acceptor DNA can be any DNA (e.g., plasmid vector) capable of being taken up by cells and integrating into genomic DNA. Suitable acceptor DNAs include viral vectors which transfect cells directly, such as recombinant retroviruses, adenovirus, adeno-associated virus, and herpes simplex virus-1. A prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding a mutated subunits of the mALDH of the invention rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464).

Another suitable acceptor vector is an adenovirus-derived vector. The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155.

Suitable adenoviral vectors derived from the adenovirus strain Ad type 5 dl324 or other strains of adenovirus (e.g., Ad2, Ad3, Ad7 etc.) are well known to those skilled in the art.

Yet another viral vector system useful as the acceptor vector is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as few as 300 base pairs of AAV can be packaged and can integrate.

Other viral vector systems that may be used as the acceptor vector in the methods of the present invention include herpes virus, vaccinia virus, and several RNA viruses.

Alternatively, the acceptor DNA can be targeted for delivery to selected cells (see e.g., U.S. Pat. No. 5,166,320) via cell-specific targeting ligands. Once taken up by cells, the acceptor DNA can be integrated into genomic DNA either randomly or selectively, for example, by homologous recombination as is well known in the art (see e.g., U.S. Pat. No. 5,614,396).

The acceptor DNA also can be introduced, for example, by microinjection and/or homologous recombination, into a host cell, embryonic stem cell, tissue, or fertilized egg.

The donor DNA can be any DNA (e.g., circular DNA) capable of being taken up by cells, either in vivo or in vitro, and capable of carrying the desired transfer (i.e., donor) DNA sequence which, for example, encodes a therapeutic gene. Suitable donor vectors include cosmids or DNA plasmids, such as recombinant bacterial or eukaryotic plasmids. The donor vector can be introduced into the host cell either in vivo or in vitro using a variety of known methods. For in vitro delivery, suitable methods include direct injection of the plasmid (e.g., microinjection), $CaPO_4$ precipitation, electroporation, cationic lipofection, or use of artificial viral envelopes. For in vivo delivery, suitable methods include intravenous, intraperitoneal and intramuscular injection of the vector. The vector can also be targeted for delivery to selected cells (see e.g., U.S. Pat. No. 5,166,320).

In a preferred embodiment of the invention, the donor DNA is introduced into the host cell in excess of the acceptor DNA to increase the frequency of DNA integration relative to excision. Integration is an intermolecular even, whereas excision is an intramolecular event. Therefore, excision naturally occurs more often than integration. To tilt the balance toward integration, the amount of donor DNA can be increased to increase the number of intermolecular exchange reactions which occur in the host cell.

In another embodiment, the acceptor and/or donor DNA also includes a selectable marker which enables the identification of clones which have undergone site-specific recombination resulting in an exchange of acceptor DNA for donor DNA. For example, the acceptor DNA can include a negatively selectable marker gene to identify cells which have lost the ability to produce a certain protein (e.g., which have lost resistance to a drug or antibiotic). Similarly, the donor DNA can include a positively selectable marker to identify cells which have incorporated the donor DNA into their genome via recombinase-mediated exchange. The marker gene can be promoterless so that it will only be expressed when integrated into the acceptor vector containing a promoter to drive its expression.

The donor and acceptor vectors each contain at least two incompatible lox sequences ("L1 and L2") so that intramolecular recombination can not occur. At the same time, the locks sequences of the donor and acceptor vectors must be able to recombine intermolecularly (e.g., L1 with a compatible L1 and L2 with a compatible L2) with one another to allow DNA exchange between the donor and acceptor vectors. In order to ensure intermolecular exchange between compatible lox sequences, the lox sequences are generally oriented in the same direction.

Incompatibility between lox sequences can be achieved, for example, by way of mutating or modifying (e.g., by nucleotide addition, deletion or substitution) one of two identical lox sequences, preferably in their spacer sequences, so that the sequences differ. Testing to determine which mutations confer incompatibility can be performed using standard mutation assays which test for the ability of the mutated and non-mutated lox sequences to recombine.

In a preferred embodiment, one of the two incompatible lox sequences is the Lox P1 sequence of the Cre/lox system of bacteriophage P1 (Hoess et al. (1990) "Nucleic Acids and Molecular Biology," Vol 4, p. 99) having the sequence shown in SEQ ID NO: 1. The Lox P1 sequence is a 34 base pair sequence which can be isolated from bacteriophage P1 by methods known in the art (see e.g., Hoess et al. (1982) *PNAS* 79:3398). The Lox P1 sequence consists of two 13 base pair inverted repeats separated by an eight base spacer sequence. Lox P1 sites can also be isolated from plasmids available from the ATCC (e.g., ATCC 53254 and 20773). Other suitable lox sequences include the Lox B, Lox L, and Lox R sequences isolatable from *E. coli* (Hoess et al. (1982), supra.). Lox sequences can also be chemically synthesized using known techniques, such as those described in the Examples below.

Accordingly, the other incompatible lox sequence can be a mutated form of the LoxP1 sequence, for example, having a point mutation in the eight nucleotide spacer sequence. In one embodiment, the point mutation is substitution of A for G at position 7 of the eight base spacer sequence of the wild type Lox P1 sequence, referred to herein as the Lox511 sequence (SEQ ID NO: 2). Accordingly, in one embodiment, the two incompatible lox sequences of the invention have the following sequences:

|         | SPACER |         |
|---------|--------|---------|
| Lox P1  | ATAACTTCGTATA ATGTAT<u>GC</u> TATACGAAGTTAT | (SEQ ID NO: 1) |
| Lox 511 | ATAACTTCGTATA ATGTAT<u>AC</u> TATACGAAGTTAT | (SEQ ID NO: 2) |

Alternatively, the donor and acceptor DNAs (e.g., vectors) contain two identical but inverted lox sequences so that intramolecular recombination between the inverted lox sequences results in an inversion of the intervening DNA, and intermolecular recombination between identical lox sequences results in exchange of donor and acceptor DNA (see FIG. 4). Moreover, because the lox sequences involved are all substantially identical, the frequency of recombination among them is the same. These features provide highly (up to 100%) efficient and stable recombinase-mediated DNA integration. In fact, in one embodiment, cells which have taken up the largest amount of donor DNA, as measured by e.g., a transient, non-integrated marker gene (e.g., green fluorescence protein), can be selected for and, among these cells, DNA exchange will be high enough that no selectable marker need be used. In these embodiments, as in those described in the preceding paragraphs, suitable inverted lox sequences include but are not limited to the LoxP 1 (SEQ ID NO:1), Lox511 (SEQ ID NO:2) and inversions thereof.

Intermolecular recombination between compatible or inverted lox sequences in the donor and acceptor vectors is catalyzed by a recombinase, such as Cre or another member of the Int family of recombinases (Argos et al. (1986) *EMBO J.* 5: 433) which have been shown to perform efficient recombination at lox sequences in both bacteria and in eukaryotic cells (Sauer et al. (1993) *Methods in Enzymology* 225: 890–900). The recombinase can be introduced into the cell along with the donor and acceptor vectors in the form of a protein or as an expressible gene encoding the protein (e.g., the Cre gene described by Sauer, B. et al. (1988) *Proc. Natl. Acad. Sci. USA* 85:5166–5170). The recombinase or recombinase gene can be introduced or transfected into the host cell before, simultaneously, or following introduction of the donor and acceptor vectors.

In one embodiment, the recombinase gene (e.g., Cre) is contained in an expression vector which is co-transfected with the donor vector following introduction and integration of the acceptor vector into the host cell. In another embodiment, the recombinase gene is contained within either the acceptor vector or the donor vector. As with the donor vector, the recombinase gene can be introduced into the host cell either in vivo or in vitro using known techniques, such as $CaPO_4$ precipitation, electroporation, cationic lipofection, use of artificial viral envelopes, microinjection (e.g., into fertilized eggs), direct injection (e.g., intravenous, intraperitoneal or intramuscular). The vector can also be targeted for delivery to selected cells (see e.g., U.S. Pat. No. 5,166,320).

The DNA which is transferred from the donor to the acceptor vector by way of the site-specific recombination method of the invention can be any DNA desired for stable integration into a host cell genome. For example, the gene can be any transgene useful, for example, in gene therapy or for diagnostic purposes. The gene can encode a desired therapeutic protein, such as α, β or δ globin, blood coagulation factors (e.g., Factors VIII and IX) gene, cell surface receptors and other desirable proteins, for example, to correct inherited deficiencies of these proteins in an individual.

Accordingly, in one embodiment, the invention can be used in vivo to create transgenic mammals and/or plants. For example, animals of human disease can be generated, particularly if multiple genes have to be expressed at well regulated levels. Transgenic animals and/or plants can be created using known techniques, such as microinjection or other methods of introducing DNA into fertilized eggs or cells (e.g., embryonic stem cells), which contain target lox sequences (e.g., inverted or incompatible) at chromosomal locations that are not subject to position effects or to desired position effects for directing expression of a gene of interest. This allows for the generation of animals and/or plants with, for example, higher resistance to disease or improved physical/functional characteristics.

In general, there are two broad types of applications for the invention depending on whether the Lox sites are integrated in the genome at random sites or at known chromosomal locations (e.g., via homologous recombination). Lox sites at random locations can be used to generate reference loci, such as loci with characteristic position-effects. For instance, the invention can be used to site-specifically integrate particular genes into reference loci favorable for strong expression in a particular tissue, or loci that confer a pan-cellular or a variegated pattern of expression. Moreover, site-specifically integrated donor DNA at known genomic locations can facilitate the systematic characterization of endogenous cis-regulatory elements and the genetic dissection of protein function via the generation of mutated versions of endogenous gene products.

Accordingly, in other embodiments, the invention provides a means for (1) the discovery and analysis of cis-acting DNA regulatory elements controlling expression and position-effects 2) the production of polypeptides of biological value by insertion of transgenes at reference loci at which expression is high or optimally inducible, (3) the development of designer proteins by insertion of multiple versions of a gene at the same locus in order to test variants in a context in which they are produced in the same amount and have the same tissue distribution, (4) the creation of animal models of human diseases (particularly those in which multiple genes must be expressed at well regulated levels), and (5) the creation of improved agricultural organisms.

Classical gene transfer technology often involves cumbersome screening procedures to identify clones or animals with appropriate levels and developmental patterns of expression. These first generation technologies are sufficient to perform simple genetic manipulations, however, they are inadequate for the implementation of complex genetic strategies to modify plants and animals by introduction of large numbers of carefully regulated transgenes to achieve a desired phenotype. For such complex genetic engineering purposes the development of rules for the creation of artificial genetic loci (AGL) is required. The compositions and methods of the present invention provide a means for creating an AGL by allowing for the production of an array of genes and regulatory elements integrated at reference genomic sites whose chromatin structure and influence on gene expression can be controlled at will by insertion of known cis-acting elements. Thus, transgenes making up an AGL can be expressed in a tissue and in a developmental stage-specific manner at levels that are totally predictable. The present invention facilitate the development of AGLs by both permitting the careful characterization of the site with different cis-regulatory elements and mediating the efficient and convenient exchange of multiple transgenes into the AGL.

Accordingly, the methods and compositions of the invention can be used for a variety of therapeutic and diagnostic applications which require stable and efficient integration of transgene sequences into genomic DNA of cells. The methods and compositions can be used to transform a wide variety of eukaryotic cells (e.g., mammalian) cells and provide the advantage of high efficiency DNA transfer.

EQUIVALENTS

Those skilled in the art will recognize, or be able to ascertain using no more than routine experimentation, many equivalents to the specific embodiments of the invention described herein. Such equivalents are intended to be encompassed by the following claims. The entire contents of all references, published patent applications and issued patents cited throughout this application are hereby incorporated by reference.

EXAMPLES

Example 1

Cre/Lox Mediated Gene Integration Using Incompatible Mutated Lox Sequences

DNA Construction and Cell Culture

DNA vectors were made using standard techniques (Sambrook, J. et al. (1989) *Molecular Cloning: A Laboratory Manual*—2nd ed Cold Spring Harbor Laboratory Press, Cold Spring Harbor, New York, USA). Oligonucleotides were synthesized by Research Genetics, Inc. Accuracy of DNA construction was verified by sequencing. LXSN retroviral vector (Miller, A. D. et al. (1989) *Biotechniques* 7:980–990) was provided by D. Miller (Fred Hutchinson Cancer Research Center, Seattle), Hygromycin B (Lupton, S. D. et al. (1991) *Mol. Cell. Biol.* 11:3374–3378) phosphotransferase gene by D. Housman (MIT, Cambridge), Herpes Simplex virus thymidine kinase (HSV-TK) gene (Lupton, supra) by M. R. Capecchi (Salt Lake City, Utah), U19 SV40T mutant gene (Renfranz, P. J. et al. (1991) *Cell* 66:713–729) by R. D. McKay (MIT, Cambridge) and G. Almazan (McGill University, Montreal), Cre recombinase gene (Sauer, B. et al. (1988) *Proc. Natl. Acad. Sci. USA* 85:5166–5170) by D. W. Ow (UC Berkeley, Albany), CD24 (Pawlink, R. et al. (1994) *Blood* 84: 2868–2877). MSCV (murine stem cell virus) retroviral vector (Hawley, P. G. et al. (1994) *Gene Therapy* 1: 136–138), pBabe retroviral vector (Morgenstern, J. P. et al. (1990) *Nucl. Acids Res.* 18:3587–3596) by R. Weinberg (MIT, Cambridge), pcDNA1 by Invitrogene Corp. and pOPRSVICAT by Stratagene, Inc. NIH3T3 cells were obtained from the ATCC, BOSC23 cells (Pear, W. S., et al. ((1993) *Proc. Natl. Acad. Sci., USA* 90:8392–8396) W. Pear and D. Baltimore (Rockefeller University, New York).

NIH3T3 cells were grown at 37° C. with 5% CO2/95% air in DMEM supplemented with 10% heat inactivated calf serum (CS), 4.5 mg/ml glucose, 2 mM glutamine, 100 IU/mi penicillin and 100 µg/ml streptomycin. For BOSC23 cells, CS was replaced by 10% heat inactivated fetal calf serum (FCS).

Cell Infection, Transfection and Selection

The packaging cell line, BOSC23, was grown as described (Pear, supra, Danos, O. et al. (1988) *Proc. Natl. Acad. Sci. USA* 85:6460–6464). Plasmid DNA's were prepared by the Qiagen procedure (Qiagen, Inc.) and transfected in BOSC23 cells using a calcium phosphate procedure (5prime:3prime, Inc.). Viral supernatants from producers were harvested and filtered as described (Pear, supra, Danos, supra). All infections were carried out in the presence of 8 µg/ml Polybrene (Sigma). Viral supenatants from BOSC23 were used to generate stable viral producers. Virus titers were estimated by infection and selection of NIH3T3 cells using standard calculations previously described (Pear, supra, Danos, supra). Detection of helper viruses was performed by a β-galactosidase mobilization assay as described (Pear, supra, Danos, supra). Selection was applied two days after infections. Standard concentrations (1×) of selection agents were 320 µg/ml for Hygromycin B (Calbiochem). Packaging NIH3T3 cells were selected with 1×, MDHF with ½× and BSMC with 2× concentrations.

Site Specific DNA Integration Using Incompatible Mutated Lox Sequences

To study the efficiency of gene integration using the Cre/lox mediated gene transfer system described herein, the following protocol was performed.

Figure 2:
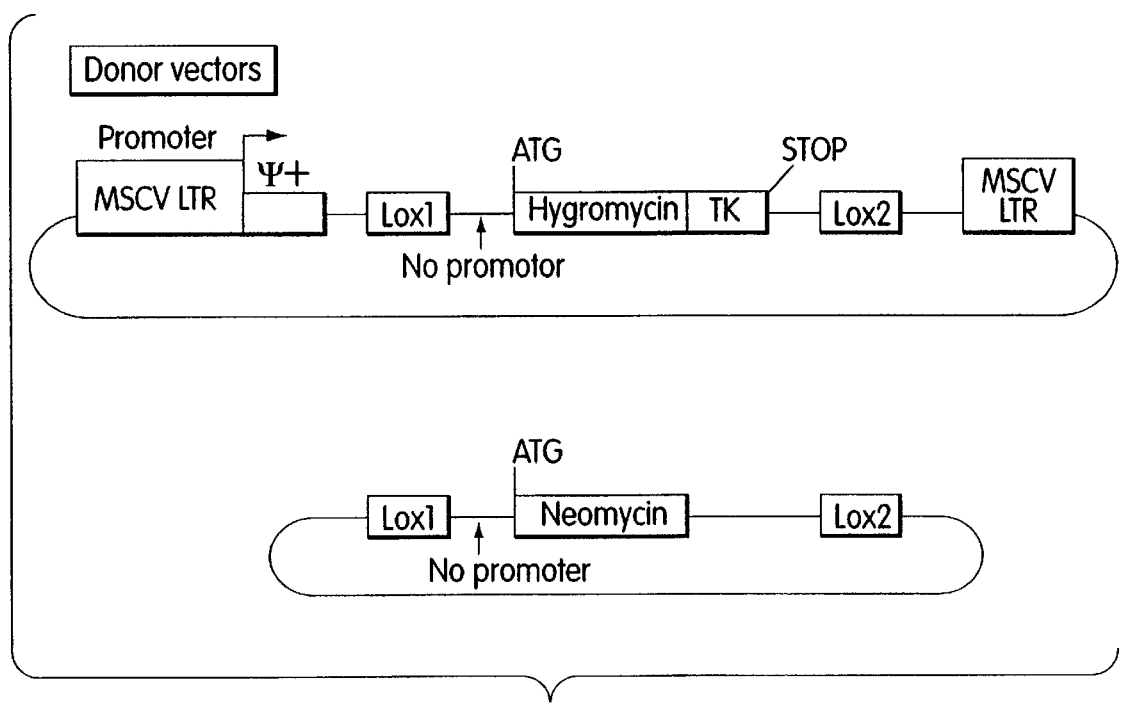
FIG. 2 is an illustration of acceptor and donor vectors containing selectable marker genes and incompatible lox sequences. Following pre-integration of the acceptor vector into a genome, the donor vector undergoes site-specific Cre-mediated recombination with the acceptor vector at the lox sequences, resulting in stable DNA exchange between the vectors.

Acceptor vectors were constructed using the MSCV retroviral vector. The vectors contained in order: the left MSCV LTR (containing promoter), followed by a lox L1 sequence, followed by a hygromycin-TK fusion gene (as a selectable marker), followed by a ox L2 sequence, followed by the right MSCV LTR (see FIG. 2). The retrovirus LTR was used as a the promoter for the hygromycin-TK fusion gene. Similar constructs were made using other selection markers such as neomycin.

The L1 and L2 lox sequences of the acceptor vector had the nucleotide sequences shown below (corresponding to SEQ ID NO: 1 and SEQ ID NO: 2). L1 is the wild type LoxP1 sequence (SEQ ID NO: 1) from bacteriophage P1 (Abremski et al. (1983) *Cell* 32: 1301–1311). L2 is a mutated form of the wild type LoxP1 sequence, referred to as Lox511, having a point substitution of A for G at position 7 of the eight nucleotide spacer region (Waterhouse et al. (1993) *Nucleic Acids Res.* 21(9):2265–2266).

|  | SPACER |
| --- | --- |
| L1 | ATAACTTCGTATA ATGTATGC TATACGAAGTTAT |
| L2 | ATAACTTCGTATA ATGTATAC TATACGAAGTTAT |

Following construction of the acceptor vector ("L1-hygromycin-TK-L2 construct"), BOSC23 cells (ecotropic packaging cells) were transiently transfected with acceptor vector using a calcium phosphate procedure (5prime:3prime, Inc.). Viral supernatants from producers were harvested and filtered as described (Pear, supra, Danos, supra). All infections were carried out in the presence of 8 μg/ml Polybrene (Sigma) Viral supernatant containing high-titer (>$10^5$ pfu/ml) retroviral vector was then used to infect host NIH 3T3 cells using the same procedures. After 48 hours in culture, the infected 3T3 cells were selected with hygromycin.

Donor vectors were constructed using pUC 19 plasmid (Yanish-Perron et al. (1985) *Gene* 33:103–119) as the backbone. The vectors contained in order: the L1 lox sequence, followed by a promoterless neomycin gene, followed by the L2 lox sequence (see FIG. 2). Similar donor vectors were made using hygromycin-TK, CD24, and B-globin genes in place of the neomycin gene. Control donor vectors were constructed using a neomycin gene with the PGK (phosphoglycerol kinase) promoter, PGK-neomycin.

Various concentrations of donor vector containing neomycin gene were co-electroporated, along with an expression vector containing the Cre recombinase gene, into the infected 3T3 cells. The concentrations of donor vector ranged from 10 μg to 200 μg. After 48 hours in culture, transformed cells were selected with neomycin. Concentrations 100 μg or more of donor vector resulted in a 10–30% integration efficiency (as measured by transfer of neomycin gene for hygromycin gene).

Different ratios of donor vector and Cre expression vector, ranging from 20:1 to 1:1 were co-electroporated into the infected 3T3 cells. All ratios resulted in the transfer of the neomycin for the hygromycin. However, a ratio of 3:1 (donor:Cre) resulted in the highest integration efficiency.

The following table provides the results of neomycin gene integration using various donor and Cre expression vectors (see FIG. 3) at a concentration of 100 μg of donor vector (DNA) at a ratio of 3 parts donor vector to 1 part Cre expression vector. Experiments E#1–4 were performed as negative controls. E#5 was the positive control.

| Cells Electroporated | Constructs Used | # Colonies (out of $10^7$ cells) |
| --- | --- | --- |
| E #1 | 3T3 | lox 1-PGKNeo-lox 2 & Control Cre expression vector | 530 |
| E #2 | 3T3 | lox 1-Neo-lox 2 & control Cre expression vector | 10 |
| E #3 | 3T3 | lox 1-Neo-lox 2 & Cre expression vector | 2 |
| E #4 | 3T3 containing lox A-hygro-TK-lox B | lox 1-Neo-lox 2 & control Cre expression vector | 21 |
| E #5 | same | lox 1-Neo-lox 2 & Cre expression vector | confluent (>$10^5$) |

E#1 used the control donor vector (see FIG. 2), lox 1-PGKNeo-lox 2 (containing the neomycin gene and a promoter) along with a control Cre expression vector (see FIG. 3) (in which the sequence encoding Cre had been deleted and replaced by a gene encoding CAT). Host cells did not contain integrated acceptor vector. Therefore, E#1 demonstrated the amount of neomycin resistance conferred by random integration of the L1-PGKNeo-L2 vector capable of expressing the neomycin gene. As expected, the conferred neomycin resistance was in the range of efficiency of integration obtained by electroporation (e.g., about 0.1% efficiency).

E#2 used donor vector (promoterless) with a control Cre expression vector. Host cells did not contain integrated acceptor vector. Therefore, E#2 demonstrated the resistance conferred in the absence of acceptor vector or Cre recombinase (i.e., in the absence of efficient recombination and gene transfer). As expected, this was very low.

E#3 used donor vector (promoterless) with a functional Cre expression vector. Host cells did not contain integrated acceptor vector. Therefore, E#3 demonstrated the resistance conferred in the absence of acceptor vector (i.e., in the absence of efficient recombination and gene transfer), but in the presence of Cre recombinase. As expected, this was very low.

E#4 used donor vector (promoterless) with a control Cre expression vector (no Cre expression). Host cells contained integrated acceptor vector (L1-hygro-TK-L2). Therefore, E#4 demonstrated the gene transfer efficiency from donor vector to acceptor vector in the absence of Cre). As expected, this was very low.

E#5 used donor vector (promoterless) with a functional Cre expression vector. Host cells contained integrated acceptor vector (L1-hygro-TK-L2). Therefore, E#5 demonstrated the gene transfer efficiency from donor vector to acceptor vector in the presence of Cre. As shown in the table above, the host cells became confluent, demonstrating a greater than 1000 fold increase in gene transfer efficiency and stability.

CONCLUSION

The foregoing studies and results demonstrate that the retroviral Cre/lox mediated gene transfer system of the present invention can be used for highly efficient and stable integration of transgenes into chromosomal DNA of mammalian cells.

Example 2

Cre/Lox Mediated Gene Integration Using Inverted Lox Sequences

Donor and Acceptor Plasmids

Plasmid constructions were performed as described above in Example 1 using standard procedures. The CMV-HYTK cassette was derived from plasmid pTgCmvhytk (Immunex, Seattle, Wash.). The CMV-EGFP and GFPuv cassettes were derived from plasmids pEGFP-N1 and pGFPuv (Clontech, Palo Alto, Calif.). The β-GFP cassette was created by replacing the CMV promoter in plasmid pEGFP-N1 by the β-globin promoter (fragment −374 to +44 relative the cap site). Cassette HS234-βGFP was produced by linking fragment HS234 (Bouhassira et al. (1997) Blood 90:3332–3344) to the β-GFP cassette. Cassette HS3-β-globZ was from pCAS3 (O'Gorman et al. 1991) Science 251:1351–1355. A series of plasmids containing a cassette flanked by Lox sites, L1 (SEQ ID NO:1) and L2 (SEQ ID NO:2), in various orientations were created. Each plasmid was designated by the Lox site 5' of the cassette, the name of the cassette and the Lox site 3' of the cassette. Inverted L1Lox site were designated as 1L.

The following plasmids were used in the studies described below: pL1-HYTK-L2, pL1-HYTK-1L, pL1-CMVEGFP-L2, pL1-Gfpuv-L2, pL2-GFPuv-L2, pL1-HS234βGFP-1L, pL1-HS3βglobZ-L2EGFP (contains EGFP 3' of the L2 Lox site).

Cre Expression Plasmid (Mammalian)

Plasmid pBS 185 (CMV-CRE) was obtained from Clontech (Palo Alto, Calif.). pSSR73 (RSV-CRE) was a gift of Dr. P. Leboulch (Harvard University, Cambridge Mass.), pMC-Cre was a gift of Klaus Rajewsky (Koln, Germany) (Gu et al. (1993) Cell 73:1155–1164).

Cre Expression Plasmid (Bacterial)

A PCR generated fragment containing the coding sequence of the CRE recombinase was cloned into the NdeI/andXhoI sites of plasmid pET23c (Novagen, Madison, Wis.) resulting in a plasmid (pET23c-CRE) that expresses a His-tagged CRE protein in induced BL21 bacteria.

CRE Purification

BL21 (DE3) Lys E bacteria (Novagen, Madison, Wis.) containing plasmid pET23c-CRE were induced with 2 mM IPTG for 2 hours, sonicated in basic buffer (50 mm NaPi pH 8, 200 mm NaCl) plus 0.05% Tween 20 and 1% lysozyme, centrifuged at 4000 g for 10 min at 4° C., and the supernatant was loaded on a Talon metal affinity Resin column (Clontech, Palo Alto, Calif.). The column was washed successively with 20 ml of basic buffer containing 0, 5 and 10 mM imidazol, and the CRE protein was then eluted with 5 ml of basic buffer containing 100 mM imidazol. In vitro CRE recombination were performed as in [18].

Cell Culture and Electroporation

Culture and DNA recombination reactions in MEL cells were performed as in (Bouhassira et al. (1997) Blood 90:3332–3344). AK-7 ES cells were cultured and selected on SNL feeder cells as described (Soriano P. (1997) Development 124:2691–2700). DNA recombination was performed by electroporating (250V, 500 uF, Biorad gene pulser, Biorad, Hercules, Calif.) $3 \times 10^6$ cells with 200 g of L1GFP1L and 30 g of MC-Cre. Selection with 3 μM gancyclovir was applied 5 days after the transfection.

GFP Expression Studies $5 \times 10^5$ cells were rinsed once in PBS and resuspended in Hank's solution containing 5% Fetal Calf Serum and 2 μM propidium iodide, and analyzed on a FACSCAN flow cytometer (Becton Dickinson, Calif.).

Site Specific DNA Integration Using Inverted Lox Sequences

The following studies were performed to determine whether the efficiency of site-specific DNA integration could be increased using two inverted lox L1 (SEQ ID NO:1) sequences, in place of the lox L1 and L2 sequences used in Example 1. Thus, the L2 site was replaced with an inverted L1 site (termed 1L). As shown in FIG. 4 (panel C), intrachromosomal recombination between two inverted Lox sites leads to inversion of the HYTK negatively selectable marker previously integrated into the genome, rather than to its excision, and therefore does not remove the sensitivity to negative selection by gancyclovir. In this system, the donor cassette integrates in one orientation in half of the clones and in the reverse orientation in the other half.

A plasmid (pL1-HYTK-1L) containing the HYTK gene flanked by two inverted but identical Lox L1 (SEQ ID NO:1) sites was created, and MEL cell lines with single integrated copies of this plasmid were produced as described above. Three clones, termed RL4, RL5 and RL6 were selected for further studies. Exchange reactions were performed as above using a plasmid in which inverted L1 Lox sites flank a GFP reporter (pL1-HS234GFP-1L). After the transfection, 12 $Gan^R$ clones per cell line were picked and analyzed by Southern blots. At loci RL4 and RL5, all 12 $Gan^R$ clones tested had undergone an exchange of the HYTK cassette for the GFP cassette (FIG. 5 (panel A)). At RL6, 11 out of 12 clones tested had undergone an exchange of the HYTK cassette for the GFP cassette. As expected, about half of the clones were in reverse orientation. These results demonstrate that DNA cassette exchange with inverted lox sites can be efficiently selected using only negative selection in MEL cells.

The same experiments were then repeated in an embryonic stem cell line: Two single copy L1-HYTK-1L tagged-loci were created and tested for cassette exchange using plasmid pL1-CMVEGFP-1L. At the first locus tested, about 50% of the 60 $Gan^R$ clones tested by Southern blot had undergone an exchange (FIG. 5 (panel B)). At the second locus the frequency of exchange was about 10%. As in MEL cells, clones in both orientations were obtained in approximately equal proportion.

Example 3

Cre/Lox Mediated Gene Integration Using no Selectable Marker

The materials and methods used in the studies described below were as described in Examples 1 and 2 above.

Typically, site specific DNA recombination systems employ an active negative selectable marker at the integration site prior to exchange. Since, in many situations, it would be advantageous to perform recombination at loci that do not contain any active genes at all, the following system was designed which does not require the presence of an active gene before or after the recombination (e.g., cassette exchange).

When no selection is applied, about 1% of the MEL cells that survive the transfection undergo recombination. To increase this frequency, a GFP reporter gene was placed in the exchange plasmid, outside the exchange cassette, and cells that expressed the highest levels of GFP were selected for to increase the proportion of selected cells which had undergone exchange. This is because the sorted cells would be the cells that have taken up the highest amount of the exchange plasmid during the transfection (FIG. 4 (panel D)).

Specifically, a plasmid containing a GFP reporter gene located outside of a LacZ exchange cassette (pLI- HS3βglobZ-L2-GFP) was created and co-transfected with a CRE expression plasmid in two lines of MEL cells (RL1 and RL3) containing pre-integrated target L1 and L2 Lox sites flanking the HYTK gene. Forty-eight hours post-transfection, the cells expressing the highest amount of GFP (0.1 percentile) were sorted individually into 96 well plates, expanded without applying any selection and tested for DNA cassette exchange. Seventy-four clones were obtained for the RL1 line and 32 for the RL3 line. The clones that had lost the HYTK gene were identified by culture in hygromycin, and the Hyg$^S$ clones were then tested by Southern blots: At locus RL1, 4% (3/74) of the clones obtained had an exchange and 12% had lost the locus without exchange, probably because of a CRE-mediated excision. At locus RL3, 16% (5/32) of the clones had an exchange and 12% had lost the locus without exchange. This demonstrates that exchange with no expressed selectable marker in the genome can be performed at relatively high frequency by simply sorting the cells that have been transfected with a large number of exchange plasmids.

Example 4

Site-Specific Integration Greatly Improves Reproducibility of Expression

The materials and methods used in the studies described below were as described in Examples 1 and 2 above.

To determine whether site-specific chromosomal integration leads to expression that is more reproducible and predictable than expression of the same cassette, randomly integrated. Mel cell clones with integration of the CMV-EGFP cassette at random sites were generated by transfection of plasmid pEGFP-N1, and compared with clones containing the CMV-EGFP cassette integrated by site-specific Cre/lox-mediated exchange at locus RL4.

Figure 3:
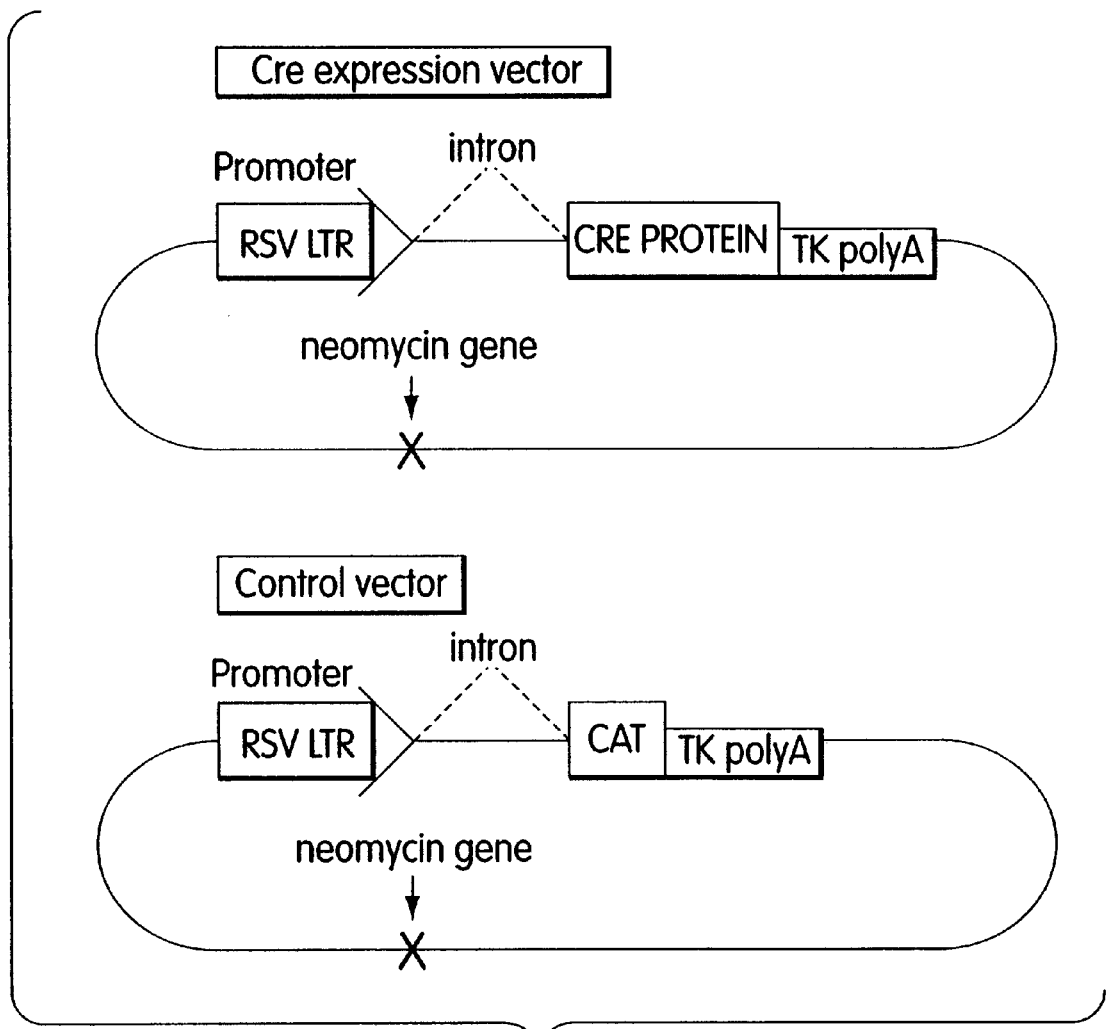
FIG. 3 is an illustration of a Cre expression vector and a control Cre expression vector.
Figure 4A:
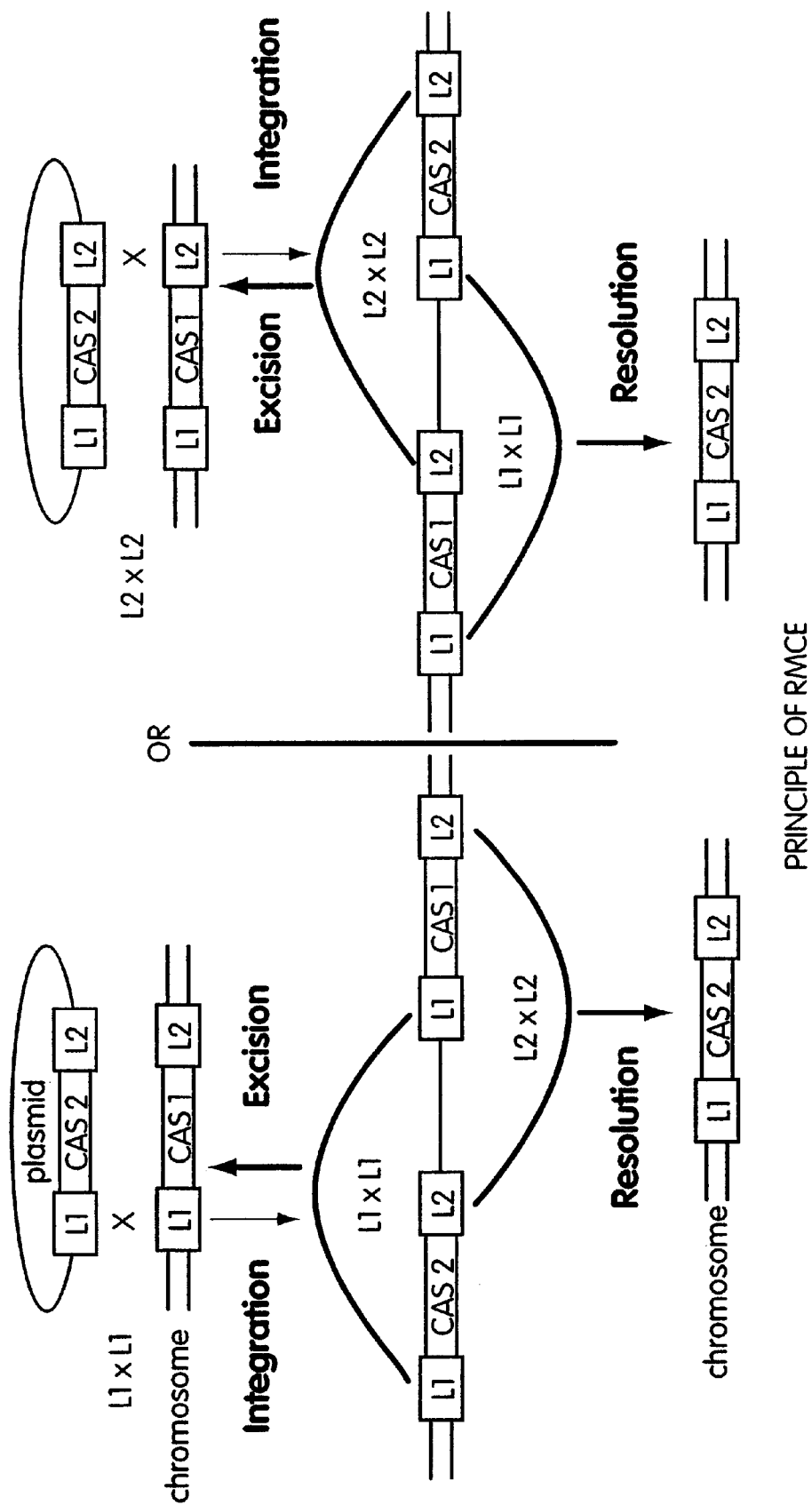
FIGS. 4A–4D is a schematic illustration of recombinase-mediated DNA cassette exchange using either incompatible exchange sequences (e.g., lox L1 and L2) or inverted exchange sequences (e.g., lox L1 and 1L). Panel A shows how site-specific chromosomal integration can be performed by exchanging a pre-integrated chromosomal cassette (cas1) with a plasmidic cassette (cas 2), using incompatible lox sequences. Recombination through the L1 site leads to plasmid integration; recombination through L2 leads to resolution of the array thus created. The end result of the recombination reaction is therefore an exchange of cassette 1 by cassette 2. This exchange is stable because the cassette is flanked by Lox sites that cannot recombine with each other. Symmetrical integration through L2 and resolution through L1 also lead to the cassette exchange. After integration the resolution step is in competition with an excision step that is the reverse of the integration step. Panel B shows how selection for the loss of the HYTK cassette can be used to identify clones which have undergone site-specific chromosomal recombination. Panel C shows site-specific chromosomal recombination using inverted Lox sites: The L2 Lox site is replaced by an inverted L1 site (1L). Excision products are eliminated because recombination between Lox sites located in cis leads to inversion of the HYTK gene rather than its excision (upper recombination). Gancyclovir selection therefore lead predominantly to the identification of exchange products (lower recombination). Exchange products in both possible orientations are obtained. Only one of several exchange pathways is depicted. Panel D shows FACS-based site-specific chromosomal recombination. A plasmid containing the CMV-EGFP reporter gene inserted outside of the exchange cassette is co-transfected (with a CRE expression plasmid) and cells that express the highest amount of GFP are sorted. Among those cells, exchange frequency is relatively high. No selectable marker on the chromosome is required before or after the exchange.
Figure 4B:
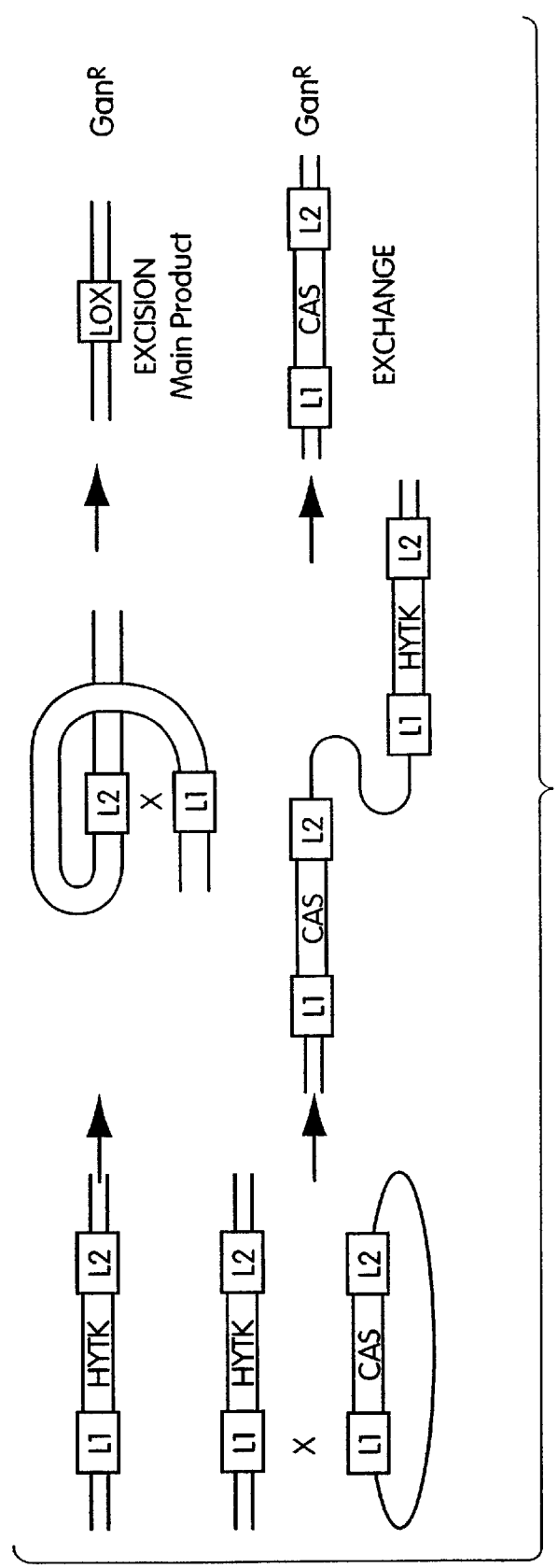
Figure 4C:
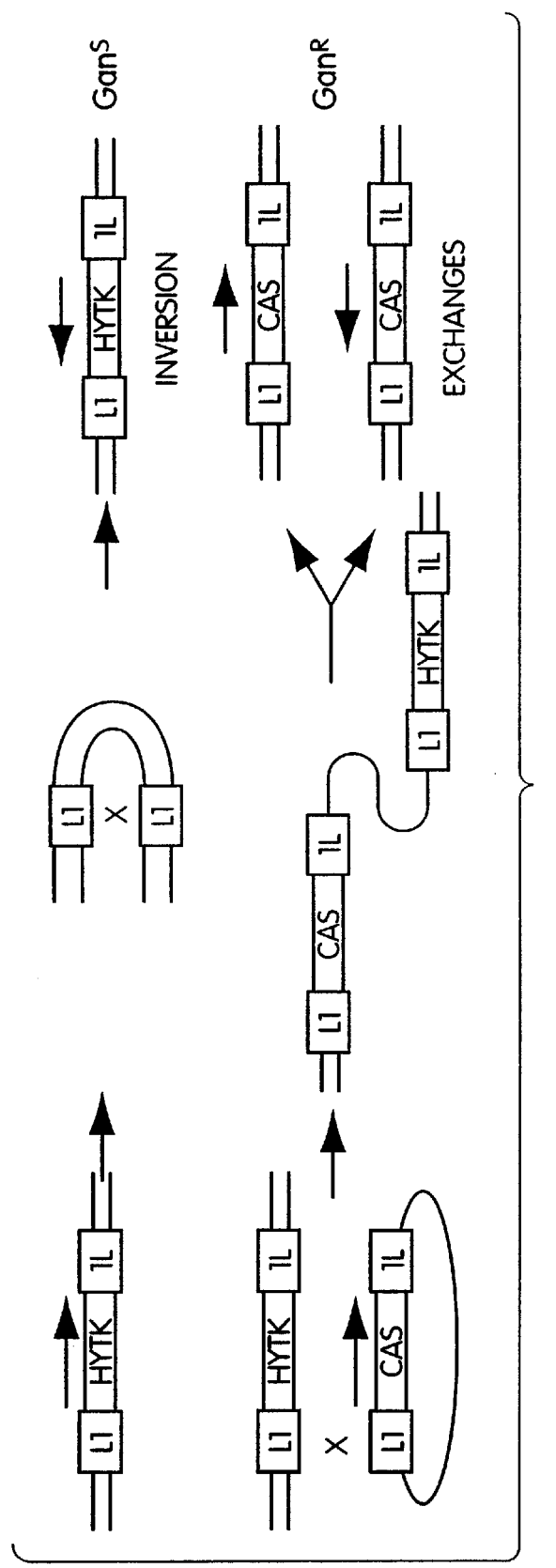
Figure 4D:
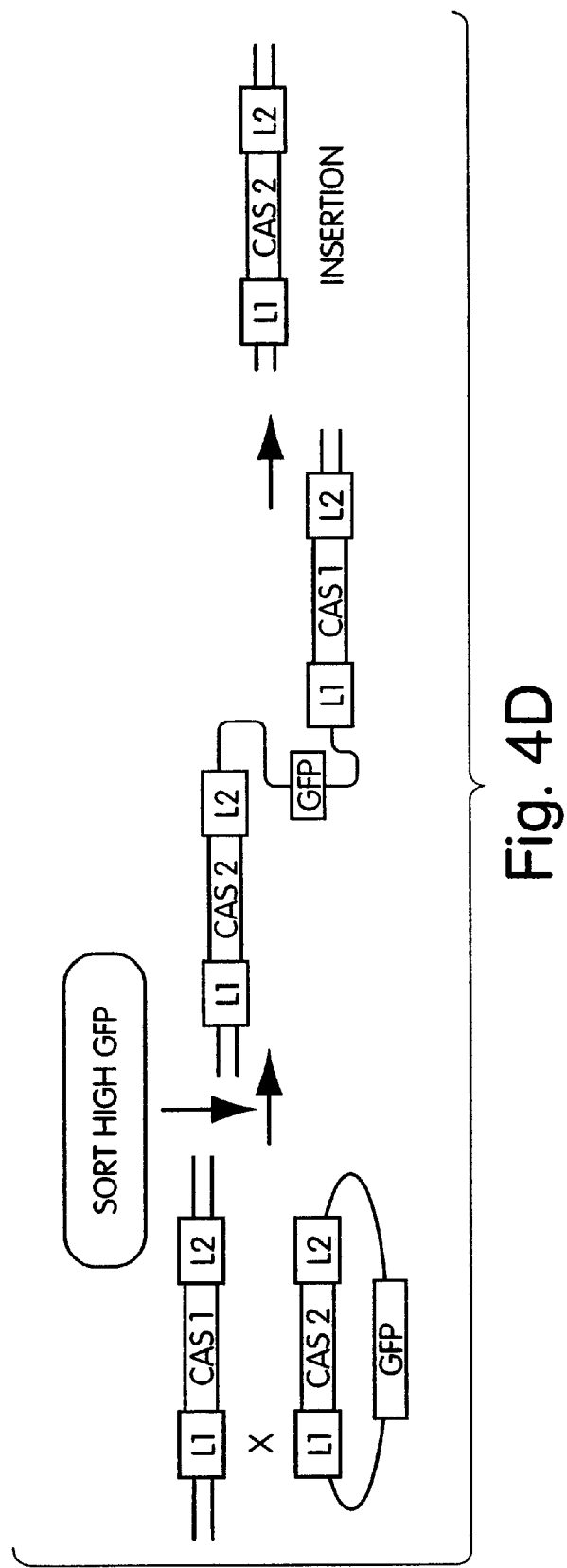
Figure 5A:
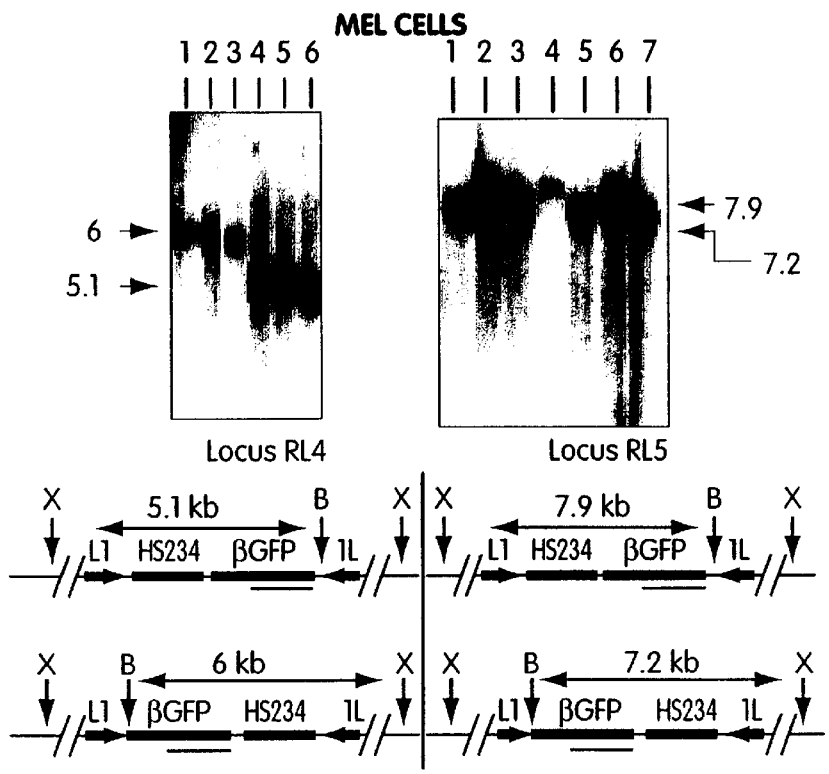
FIGS. 5A–5D show Southern blots confirming site-specific chromosomal recombination in MEL and ES cells. Panel A is an autoradiogram illustrating the exchange of the HYTK gene with the HS234βGFP cassette at two loci in MEL cells. Lanes 1 to 6 in the left panel, and lanes 1 to 7 in right panel, contain genomic DNA from $Gan^R$ resistant clones digested with EcoRV and Bgl II and probed with a fragment encompassing the EGFP coding sequence. Two bands (6.1 and 5.1 at RL4 or 7.9 and 7.2 kb at RL5) were observed per locus demonstrating insertion in both possible orientations. B=BglII; X=EcoRV or BglII. Panel B is an autoradiogram illustrating the exchange of the HYTK gene with the HS234βGFP cassette at two loci in ES cells. Lanes 1 to 7 in the left panel contain genomic DNA from $Gan^R$ resistant clones digested with HindIII and probed with a fragment encompassing the EGFP coding sequence. The right panel is a blot of the left panel stripped and re-probed with a fragment encompassing the CMV promoter. As expected, clones in both orientations were obtained. Panel C shows recombinase-mediated DNA cassette exchange using no selectable marker. Left panel, lanes 1 to 3, and right panel, lanes 1 and 2, contain genomic DNA digested with BclI and probed with a fragment encompassing the human β-globin promoter; lane C contain control DNA. As expected, all exchanges were in the same orientation. Bc=BclI. Panel D shows random (uncontrolled) integration of Cassette CMV-EGFP: Lanes 1 to 9 contain genomic DNA digested with AflII probed with the EGFP coding sequence. Bands of all sizes and intensity characteristic of uncontrolled integration are shown.
Figure 5B:
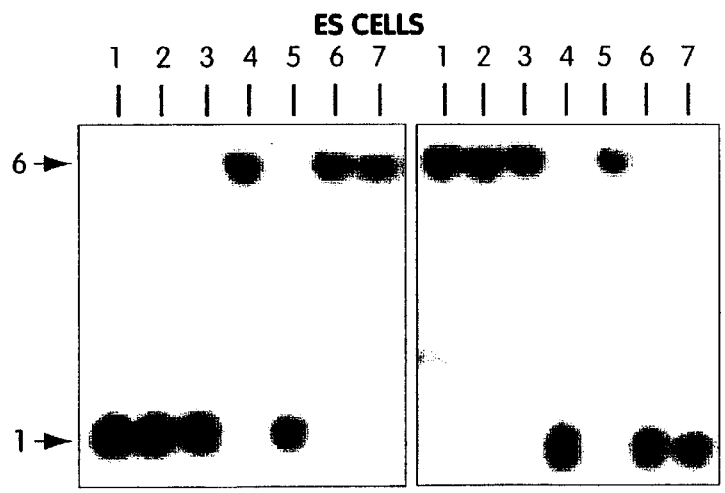
Figure 5C:
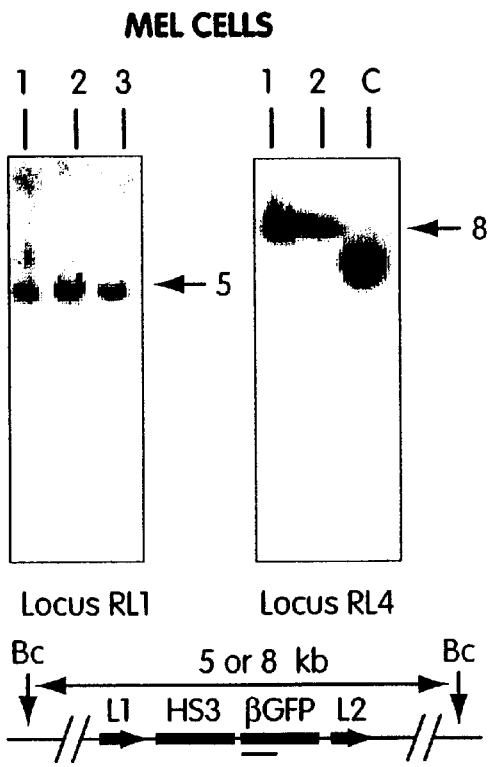
Figure 5D:
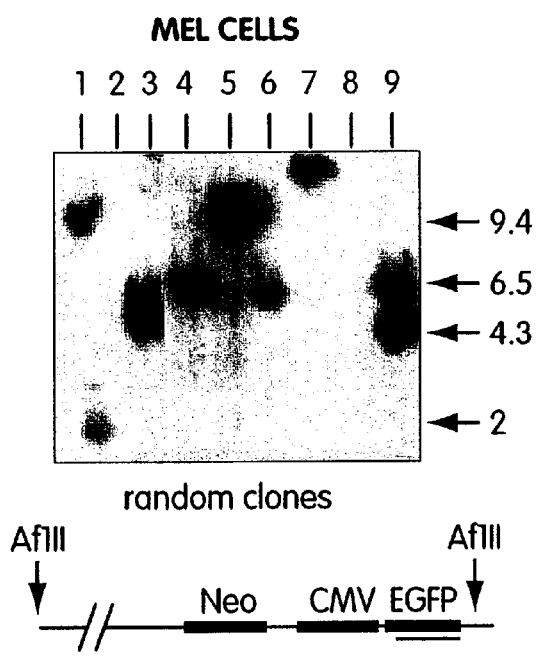
Figure 6:
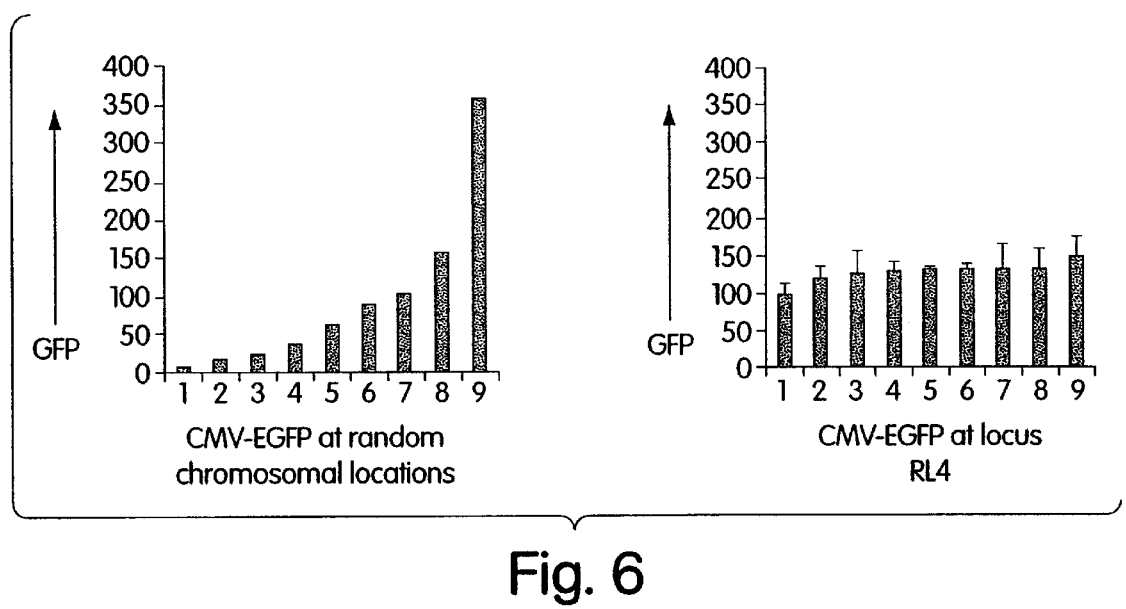
FIG. 6 is a chart showing expression levels of GFP at pre-selected locus and at a random locus: GFP expression of nine independent clones with the CMV-EGFP cassette integrated at 9 uncontrolled random loci (left panel) or at the same pre-selected locus (right panel) was analyzed by FACS. The y-axis represents the mean linearized GFP fluorescence. The results show that site-specific integration considerably diminishes the variability of expression typically observed in stable transfection studies.

Southern blots revealed that most of the random clones contained multiple integrated copies (FIG. 5 (panel D)) and that, as expected, the clones that had undergone site-specific exchange had integration in both possible orientations. Nine random clones and nine site-specific clones with integration in one of the two possible orientations were analyzed for expression by flow cytometry (FIG. 3). Mean levels of green fluorescence for the random clones varied from 5.3 (which is similar to untransfected controls) to 357.5. The average was 94.1+/−103.5. Mean levels of fluorescence for the site-specific clones varied from 100.1 to 147.4. The average was 127.8+/−11.9. Although the average expression of the two types of clones were similar, the 10-fold difference between their standard deviations clearly demonstrates that expression levels of clones integrated at the same locus by site-specific recombination are much less variable than those of randomly integrated clones. Similar results were obtained at the 5 other targeted, site-specific loci that were tested.

The highly reproducible expression observed when site-specific clones were tested in the absence of any selective pressure at the locus suggests that controlling the integration site and therefore eliminating position-effects permits meaningful comparisons of multiple transgenes individually integrated at a particular genomic site.

CONCLUSION

Overall, the studies described above demonstrate that highly efficient methods of Cre/lox-mediated recombination, such as those described in the studies above, can be used to achieve site-specific recombination with no incoming selectable marker and in a defined orientation. These methods also can be used to achieve multiplex integration of transgenes (Sauer B. (1996) *Nucleic Acids Res.* 24:4608–4613) sequentially at the same site or at multiple independent sites using multiple pairs of lox sites, either as heterospecific pairs or inverted as described herein. These methods also can be used in combination with FLP (Seibler et al. (1998) *Biochem.* 37:6229–6234)-mediated DNA exchange systems.

Prior to the present invention, expression of experimental constructs in mammalian cells or transgenic animals was difficult to control because it is markedly influenced by position effects. This limited both the analysis of cis-DNA regulatory elements for transcription and replication and the physiological analysis of proteins expressed from transgenes. The novel compositions and methods of the present invention solve these problems by permitting the exchange of DNA (e.g., containing a negative selectable marker pre-localized on the chromosome with a transgene via a Cre-mediated double recombination between inverted or mutated, incompatible Lox sites. Integration efficiency of close to 100% of negatively selected cells can be achieved. In addition, the present invention provides a way of achieving site-specific recombination within genomic DNA with no selection at all, except for cells that have taken up plasmid transiently.

The foregoing studies demonstrate that integration of a transgene at a given genomic site leads to reproducible expression. Therefore, the compositions (e.g., DNA vectors) and methods of the present invention can be used to develop artificial genetic loci that impart specific and reproducible regulation of transgenes in higher eukaryotes. This should facilitate the analysis of cis-regulatory DNA elements governing expression and position effects, improve control over the physiological effects of transgenes, and accelerate the development of animal models for complex human diseases.

What is claimed is:

1. A method of achieving site-specific recombination in a selected cell comprising, in any order, the steps of:
   (a) introducing into the cell an acceptor DNA which integrates into the genome of the cell, the acceptor DNA comprising two compatible inverted nucleotide sequences which undergo recombination when catalyzed by a recombinase;
   (b) introducing into the cell a donor DNA comprising the same two compatible inverted sequences contained in the acceptor DNA; and
   (c) introducing into the cell the recombinase which catalyzes recombination between the sequences.

2. The method of claim 1 wherein the acceptor DNA further comprises a negatively selectable marker flanked by two inverted lox sequences.

3. The method of claim 1 wherein the donor DNA introduced into the cell is present in excess of the acceptor DNA.

4. The method of claim 1 wherein the recombinase is introduced into the cell by transfecting the cell with a gene expressing the recombinase.

5. The method of claim 1 wherein the recombinase is introduced into the cell in the form of a protein.

6. The method of claim 1, wherein the two compatible inverted sequences comprise nucleotide sequences selected from the group consisting of: (a) SEQ ID NO:1 and its corresponding inverted sequence; and (b) SEQ ID NO:2 and its corresponding inverted sequence, and wherein the recombinase is Cre.

7. The method of claim 1 wherein the donor DNA further comprises a transgene encoding a therapeutic protein.

8. The method of claim 1 wherein the donor DNA further comprises a positively selectable marker.

9. The method of claim 1 wherein the cell is a mammalian cell.

10. The method of claim 1, wherein the recombinase is Cre recombinase.

11. The method of claim 1, wherein the recombinase is Flp recombinase.

12. The method of claim 1, wherein the two compatible inverted sequences comprise nucleotide sequences selected from the group consisting of: (a) SEQ ID NO:1 and its corresponding inverted sequence; and (b) SEQ ID NO:2 and its corresponding inverted sequence.

13. The method of claim 1, wherein the acceptor DNA is integrated into the genome using a retroviral vector.

14. The method of claim 1, wherein the acceptor DNA is integrated into the genome by homologous recombination.

15. The method of claim 2 further comprising the step of negatively selecting cells which have undergone site-specific recombination.

16. The method of claim 7 wherein the therapeutic protein is β-globin.

* * * * *

UNITED STATES PATENT AND TRADEMARK OFFICE
CERTIFICATE OF CORRECTION

PATENT NO. : 6,534,314 B1
APPLICATION NO. : 09/293303
DATED : March 18, 2003
INVENTOR(S) : Eric Bouhassira et al.

It is certified that error appears in the above-identified patent and that said Letters Patent is hereby corrected as shown below:

Please delete the paragraph titled 'GOVERNMENT FUNDING' encompassing column 1, lines 14-17:

"This invention was made with government support under grants HL38655, HL 554350, DK54071-020 and HL07556, all of which were awarded by the NIH. The United States government has certain rights in the invention."

and replace with:

--This invention was made with government support under Grant No. HL055435 awarded by the National Institutes of Health. The government has certain rights in this invention.--

Signed and Sealed this
Thirteenth Day of November, 2012

David J. Kappos
*Director of the United States Patent and Trademark Office*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 34 base pairs
      (B) TYPE: nucleic acid

```
            (C) STRANDEDNESS: single
            (D) TOPOLOGY: linear (ii) MOLECULE TYPE: DNA (xi) SEQUENCE DESCRIPTION: SEQ ID NO:1:

ATAACTTCGT ATAATGTATG CTATACGAAG TTAT                                    34

(2) INFORMATION FOR SEQ ID NO:2:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:2:

ATAACTTCGT ATAATGTATA CTATACGAAG TTAT                                    34
```